United States Patent
Brown

(10) Patent No.: US 6,203,816 B1
(45) Date of Patent: *Mar. 20, 2001

(54) TISSUE FACTOR BASED PROTHROMBIN TIME REAGENT

(75) Inventor: Scott M. Brown, Scripps Ranch, CA (US)

(73) Assignee: Corvas International, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/427,683

(22) Filed: Apr. 24, 1995

Related U.S. Application Data

(63) Continuation of application No. 08/126,668, filed on Sep. 22, 1993, now abandoned, which is a continuation of application No. 07/612,118, filed on Nov. 13, 1990, now abandoned.

(51) Int. Cl.[7] ................................................. A61K 9/127
(52) U.S. Cl. ........................ 424/450; 264/4.1; 264/4.3; 436/69; 514/21
(58) Field of Search ............................ 424/450, 812; 264/4.1, 4.3; 436/69, 829; 514/21

(56) References Cited

U.S. PATENT DOCUMENTS

| | | | |
|---|---|---|---|
| 3,179,567 | * | 4/1965 | Owren .................. 530/381 |
| 4,737,276 | * | 4/1988 | Adamich .............. 210/96.2 |
| 4,761,288 | * | 8/1988 | Mezei .................... 424/450 |
| 4,857,319 | * | 8/1989 | Crowe et al. .......... 424/450 X |
| 4,865,984 | * | 9/1989 | Nemerson ............. 435/288 |
| 4,981,685 | * | 1/1991 | Healey ................. 424/92 |
| 5,223,427 | * | 6/1993 | Edgington ............. 435/240.27 |

OTHER PUBLICATIONS

Anchordoguy, Cryobiology 24, pp. 324 1987.*

Deamer et al. Liposome prep. methods & mechanism, Chap. I, 1983, pp. 27–51.*

Journal of Parenteral Science and Technology, Wang et al., 42 (S2) pp. 53–526.*

Neugebauer, J., *A Guide to the Properties and Uses of Detergents in Biology and Biochemistry*, pp. 5–6, 27 and 35, (Calbiochem–Novabiochem, 1988).

* cited by examiner

Primary Examiner—Gollamudi S. Kishore
(74) Attorney, Agent, or Firm—Lyon & Lyon LLP

(57) ABSTRACT

The present disclosure relates to novel liposome compositions in which tissue factor is incorporated and methods for their preparation. The composition of the phospholipids in the liposomes has been adjusted to allow maximum coagulant activity and sensitivity to extrinsic coagulation factors of the incorporated tissue factor.

7 Claims, 2 Drawing Sheets

TISSUE FACTOR BASED PROTHROMBIN TIME REAGENT

This application is a continuation of application Ser. No. 08/126,668, filed Sep. 22, 1993, now abandoned, which is a continuation of application Ser. No. 07/612,118, filed Nov. 13, 1990 now abandoned.

BACKGROUND OF THE INVENTION

1. Field of the Invention

The present invention relates to a prothrombin time (PT) reagent using purified, reconstituted natural or recombinant human tissue factor (rTF). More particularly, the invention relates to the reconstitution of tissue factor into phospholipid vesicles to produce a tissue factor based PT reagent. Such a reagent allows specific monitoring of oral anticoagulant therapy and deficiencies in the extrinsic pathway of coagulation.

2. Related Art

In 1935, thromboplastin (procoagulant tissue factor) use was first described in a one stage PT test (Quick, *J. Biol. Chem.*, 109:73–74, 1935). This test employed thromboplastin derived from mammalian tissue and a standard curve prepared with dilutions of pooled normal human plasma. The modern version of this test is easy to perform and can be automated. The PT test is the most commonly performed assay in the coagulation laboratory. Variants of this test have a number of uses (White, et al., *Hemostasis and Thrombosis, Basic Principles and Clinical Practice*, Coleman, et al., eds., J.B. Lippencott Co., Philadephia, pp. 1048–1060, 1987). One use is to assess deficiencies in the extrinsic pathway of coagulation (Factors VII, X, V, and prothrombin). A second use is to monitor patients undergoing long term oral anticoagulant therapy for disorders such as recurrent venous thrombosis and cancer. A third use is to evaluate liver dysfunction.

The therapeutic range of anticoagulant therapy is based on the avoidance of bleeding and thrombolic complications. When monitoring oral anticoagulant therapy, as well as for a variety of other conditions by the PT test, an elongation of prothrombin time by a factor of 2 is most desirable for long term therapy (O'Reilly, *Hemostasis and Thrombosis, Basic Principles and Clinical Practice*, Coleman, et al., eds., J.B. Lippencott Co., Philadephia, pp. 1367–1372, 1987). This elongation factor is defined as the prothrombin ratio (PR) and is calculated by dividing the PT of a patient plasma by the PT of a pool of plasmas from normal individuals. A higher PR indicates a more sensitive PT reagent. The benefits of a more sensitive reagent for monitoring anticoagulation therapy is the use of lower doses of anticoagulant drug. These lower doses still provide adequate protection against thromboembolic disease while minimizing bleeding complications.

Several reagents for determining PT times are continually available. These include Thromborel S (Curtis Matheson Scientific, Inc., Yorba Linda, Calif.) and Simplastin (Organon Teknika Corp., Charlotte, N.C.). These reagents yield very different PT times for the same patient plasma with Thromborel S exhibiting longer times than Simplastin. Lower doses of anticoagulant drug are required to maintain extended PT times (high PR) when the PT times are monitored using Thromborel S instead of Simplastin.

A need exists for an even more sensitive tissue factor based PT reagent to monitor anticoagulant therapy and other conditions. The present invention provides just such a sensitive reagent with its highly desirable PR.

SUMMARY OF THE INVENTION

The present invention relates to liposome compositions and methods for their preparation with tissue factor incorporated in the lipid bilayer. The composition of the phospholipids in the liposomes has been adjusted to allow maximum coagulant activity and sensitivity to extrinsic coagulation factors of the incorporated tissue factor. In the preferred aspect, the method of the invention utilizes the zwitterionic detergent {3-[(3-cholamidopropyl)-dimethylammonio]-1-propanesulfonate} (CHAPS) to solubilize highly purified phospholipids. Tissue factor, also solubilized in CHAPS, is added with a carrier protein and the detergent removed by dialysis. Liposomes with tissue factor reconstituted into the lipid bilayer are formed spontaneously as the detergent concentration is lowered during dialysis.

DETAILED DESCRIPTION OF THE INVENTION

Figure 1:
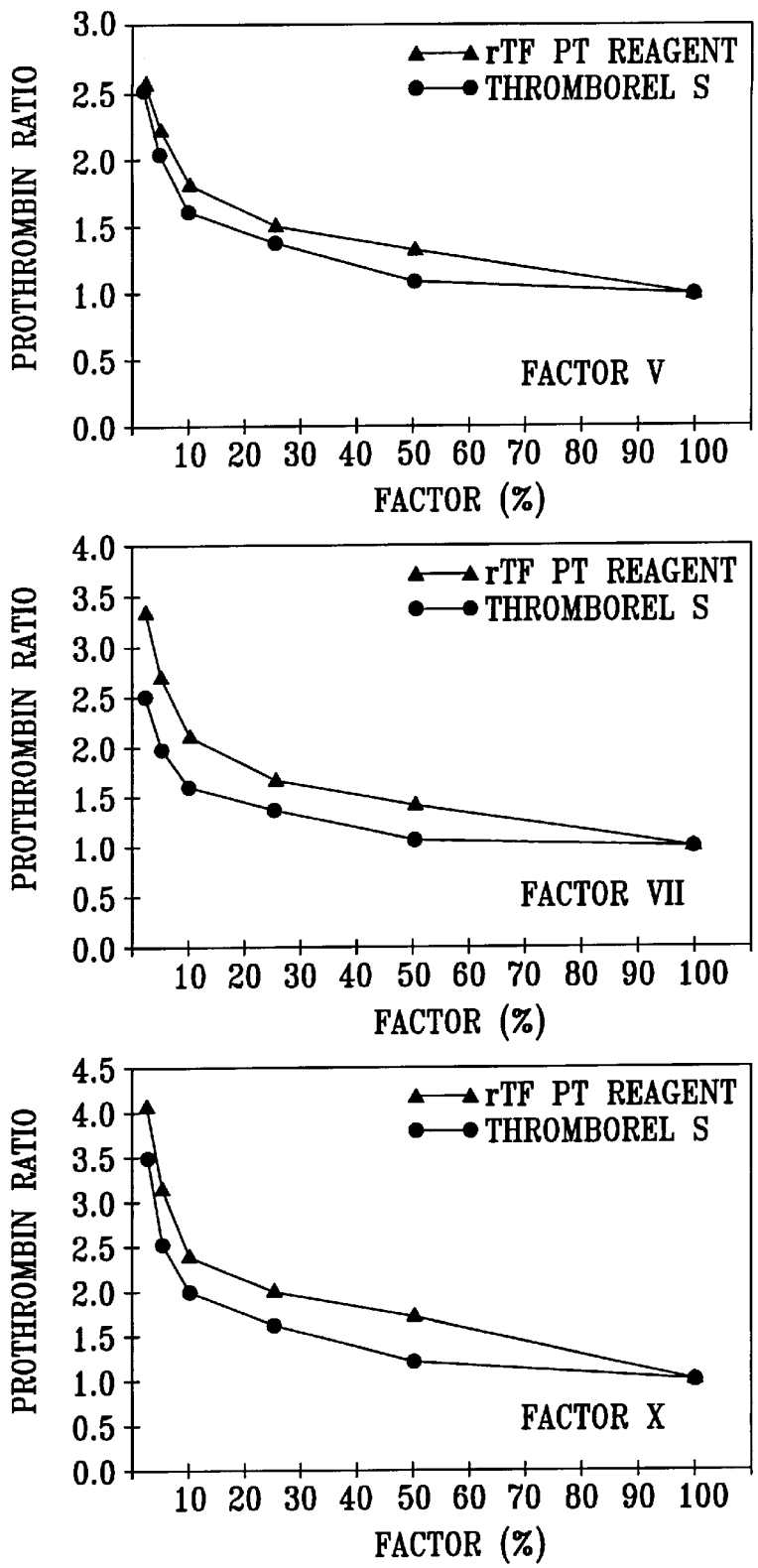
FIG. 1 shows the prothrombin ratios of PT reagents, rTF PT reagent and Thromborel S as a function of percent factor activity.

The phospholipids phosphatidylcholine (PC), phosphatidylethanolamine (PE), and phosphatidylserine (PS) that are used with the invention may come from any natural or synthetic source. For example, PC and PE may be obtained from egg yolk, and PS may be obtained from animal brain or spinal chord. The phospholipids, obtained from the manufacturers in organic solvent, are mixed to yield the appropriate composition. An antioxidant such as butyrated hydroxytoluene is added to reduce alkyl chain peroxidation, and the organic solvent is removed by evaporation. The dried lipids are solubilized in aqueous detergent. This aqueous solution, besides including detergent (eg. CHAPS or any of the alkylglucopyranosides such as octyl beta-D-glucopyranoside and octyl beta-D-thioglucopyranoside), may also include buffers (eg. HEPES, Tris, phosphate, etc.), various salts (eg. NaCl, KCl, etc.), carbohydrates (eg. trehalose, maltose, glucose, etc.), and the like. The tissue factor to be reconstituted may be natural or recombinant in nature.

In the preferred method the phospholipids are combined in a mole ratio of PC:PE:PS of 7.5:1:1 with 0.1% BHT (by weight) and the organic solvent removed. The phospholipids are solubilized at 20 mg/ml in 20 mM Tris, pH 7.5, 150 mM NaCl, (TBS) containing 100 mM CHAPS. Tissue factor and bovine gamma globulin carrier protein are added and sufficient TBS containing 150 mM trehalose is added to adjust the final concentrations of tissue factor to 10 ug/ml, bovine gamma globulin to 1 mg/ml, phospholipid to 4 mg/ml and CHAPS to 20 mM. The resulting clear, colorless solution requires no vortexing or sonicating to ensure co-solubilization. The detergent can be removed in any number of ways that result in stable liposomes. The preferred method utilizes dialysis in dialysis membrane tubing against TBS containing 150 mM trehalose and 0.05% $NaN_3$. Other methods of detergent removal may include, but are not restricted to, removal by tangential flow diafiltration, cross flow hollow fiber filtration, and removal by a hydrophobic chromatographic resin. The resulting liposomes containing tissue factor are made to 5 mM $CdCl_2$. The now fully active liposomes are diluted with 50 mM Tris, pH 7.5, 75 mM trehalose, 10 mM $CaCl_2$ before lyophilization.

An additional method also involves detergent solubilized phospholipids but requires no dialysis or detergent removal methods. Tissue factor is active in the mixed detergent-phospholipid micelles formed in this system. Phospholipids are dissolved to 20 mg/ml in 50 mM octyl beta-D-thioglucopyranoside (OTG). Carrier protein, TF, and $CdCl_2$ are added as described above and the mixture diluted with buffer to yield final concentrations of TF at 10 ug/ml, bovine gamma globulin at 1 mg/ml, $CdCl_2$ at 5 mM, phospholipids at 4 mg/ml, and OTG at 10 mM.

The methodology employed in the practice of the invention is more specifically described in the examples below.

EXAMPLE 1

PC, PE, and PS were obtained in chloroform solution from Avanti Polar Lipids, Alabaster, Ala., or Calbiochem Corp., La Jolla, Calif. in sealed glass ampules and stored under $N_2$ at −20° C. CHAPS and other detergents were obtained from Calbiochem. Tris base was purchased from BioRad, Richmond, Calif.; all other chemicals were acquired from Sigma, St. Louis, Mo.

Phospholipids were prepared for resolubilization as follows. PC, PE, and PS were warmed to room temperature and combined in a suitable tube or flask at a mole ratio of 7.5:1:1 (PC:PE:PS, respectively). The antioxidant butyratedhydroxytoluene (BHT), dissolved in chloroform, was added to the mix of phospholipids at a weight ratio of 0.1% (BHT:total phospholipids). Organic solvent was removed by evaporation under a stream of dry nitrogen or under reduced pressure in a rotary evaporator. Residual organic solvent was eliminated by pumping an additional 1 hour at room temperature on a lyophilizer pump at a pressure of 10 um or less. Phospholipids were dissolved to 20 mg/ml in 20 mM Tris, pH 7.5, 150 mM NaCl (TBS) containing 100 mM CHAPS.

Tissue factor (TF) was purified from cell lysates using the following method. Cells producing TF were washed with TBS and resuspended to $2 \times 10^7$/ml in TBS containing 0.25% Triton X100, 10 ug/ml soybean trypsin inhibitor, and 1 mM EDTA. After incubation for 30 min at 4° C., the cellular debris was removed by centrifuging for 20 min at about 5000×g at 4° C. The clarified lysate was diluted 2.5-fold with TBS to reduce the Triton concentration to 0.1% and passed through an immunoaffinity resin containing a covalently coupled monoclonal antibody directed against TF. The resin bed was washed with 2 to 3 bed volumes of TBS+0.1% Triton X100, 2 to 3 volumes 20 mM Tris, pH 7.5, 0.5 M NaCl, 0.1% Triton X100, and finally 2 to 3 bed volumes 0.5 M NaCl, 0.1% Triton X100. The bound protein was eluted from the resin with 0.1 M glycine, pH 2.5, 0.1% Triton X100. Fractions collected after the buffer was changed to glycine were neutralized immediately with an appropriate volume of 1 M Tris, pH 8. TF was found in those fractions immediately surrounding the point where the pH of the column effluent changed. The fractions containing TF were pooled, dialyzed against 20 mM Tris, pH 8, 0.1% Triton X100, and concentrated by binding the TF to a small bed volume DEAE Trisacryl column (IBF Biotechniques, Columbia, Md.). The Triton X100 was replaced with CHAPS by washing the resin bed with at least 10 bed volumes of 20 mM Tris, pH 8 containing 10 mM CHAPS. The TF was eluted with a single step of 0.5 M NaCl in 20 mM Tris, pH 8, 10 mM CHAPS.

EXAMPLE 2

Resolubilized phospholipids at 20 mg/ml in TBS+100 mM CHAPS were combined with immunoaffinity purified TF and bovine gamma globulin. Additional TBS containing 150 mM trehalose was added to yield final concentrations of 4 mg/ml phospholipid, 10 ug/ml TF, 1 mg/ml bovine gamma globulin and 20 mM CHAPS. This clear, colorless solution was placed in dialysis membrane tubing (Spectrapore®, Spectrum Medical Industries, molecular weight cutoff of 12,000 to 14,000) and dialyzed for at least 30 hours at room temperature against TBS containing 150 mM trehalose and 0.05% $NaN_3$. After dialysis the volume of the dialysate was determined and adjusted back to the original volume if required with dialysis buffer. $CdCl_2$ was added to a final concentration of 5 mM and the solution was incubated at 37° C. for 2 hours. The liposomes were then diluted to a working conentration with 0.1 M Tris, pH 7.5, 150 mM trehalose to yield a solution containing TF at approximately 1 to 2 ug/ml, phospholipids at approximately 400 to 800 ug/ml, and bovine gamma globulin at 50 to 100 ug/ml.

Prothrombin times were determined as follows. One hundred ul of plasma and 100 ul of diluted liposomes were placed in the sample well of a coagulometer. The instrument added 100 ul 20 mM $CaCl_2$ and automatically determined the prothrombin time. The results are presented in Table I. The following points can be made from the data:

(1) a wide range of phospholipid mole ratios in the liposomes is acceptable for TF mediated initiation of the clotting mechanism, and (2) the liposomes require a phospholipid component carrying a net negative charge such as PS for TF-induced clotting activity.

Although the control plasmas used in Table I are designed to simulate plasmas from patients undergoing oral anticoagulant therapy, prothrombin times obtained using these plasmas do not indicate a deficiency in any one coagulation factor, but reflect a depression of the activities of several factors. An example of how the rTF PT reagent responds to reduced levels of several individual factors involved in the extrinsic coagulation pathway is presented in FIG. 1. The rTF PT reagent used to generate these data was prepared as described above with a phospholipid mole ratio of 10:1:1 (PC:PE:PS, respectively). The prothrombin ratios shown in FIG. 1 generally increase as the percent factor activity supplied by the normal human pool (NHP) decreases.

Prothrombin ratios were calculated in the following manner. Normal human plasma pool was diluted 1:2, 1:4, 1:10, 1:20, and 1:40 with 0.15 M NaCl to yield 50, 25, 10, 5, and 2.5% factor activity. Factor deficient plasma samples (Thromboscreen, Curtis Matheson Scientific, Inc.) were rehydrated as suggested by the manufacturers and were used undiluted. Lypholized rTF PT reagent was rehydrated with distilled water, swirled, and allowed to stand for at least 15 minutes at room temperature. The reagent was swirled again just before use. Thromborel S was rehydrated and handled according to manufacturer's recommendation. One hundred ul diluted NHP and 100 ul factor deficient plasma were placed in a coagulometer sample well. PT reagent (200 ul) was added by the instrument and the PT time was determined. The PR was calculated by dividing the factor deficient PT times by the PT time obtained with undiluted NHP and was plotted against the percent of factor supplied by the NHP.

A PT reagent that exhibits a higher PR than another PT reagent at the same normal plasma pool dilution is said to be the more sensitive reagent. At all dilutions, with all of the factor deficient plasmas tested, the PR obtained using the rTF PT reagent is higher than that obtained using Thromborel S. These data suggest that liposomes containing rTF are more sensitive to specific factor depletion than is Thromborel S, which is one of the most sensitive commercially available PT reagents.

Alternatively the detergent can be removed by tangential flow diafiltration using, for example, a Pyrosart or Ultrasart filter unit (Sartorius Corp., Bohemia, N.Y., molecular weight cutoff of 20,000) and TBS containing 150 mM trehalose as the dialysis buffer. Approximately 95 to 100% of the CHAPS can be removed by passing 10 volumes of dialysis buffer through the device. Hydrophobic chromatographic resins such as Amberlite XAD-2 (Rohm and Haas Co., Philadelphia, Pa.) or Bio-Beads SM-2 (BioRad, Richmond, Calif.) can also be used to remove the detergent, either in direct contact with the phospholipid solution or separated from it by a dialysis membrane. The rate of removal is proportional to the ratio of the volumes of the detergent-phospholipid solution and the chromatographic resin beads. The rate of removal can be easily adjusted from 99% removal in 1 hour at room temperature (1:1 ratio) to 99% in 20 hours (5:1, detergent solution:beads, respectively).

EXAMPLE 3

Figure 2:
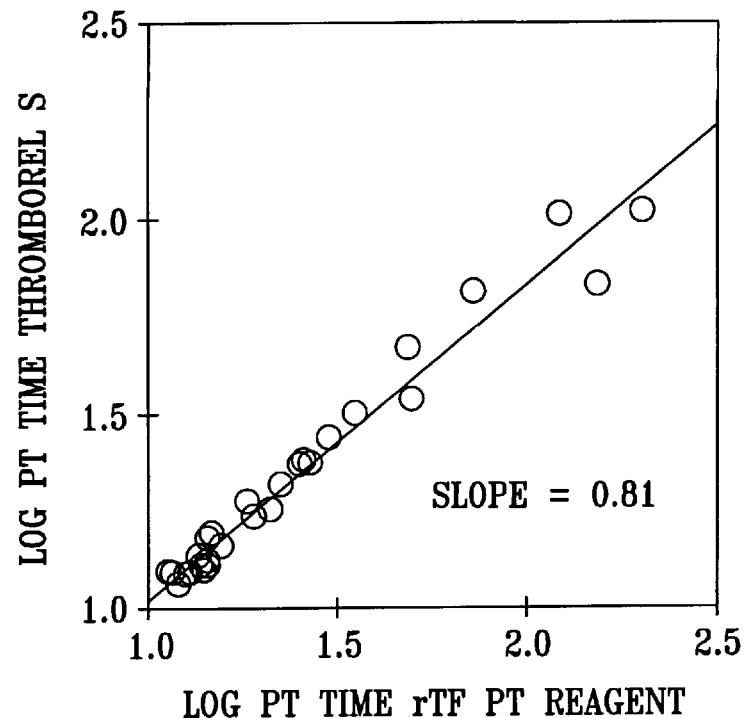
FIG. 2 shows the relative sensitivities of PT reagents to plasmas from patients undergoing oral anticoagulant therapy.
Figure 2:
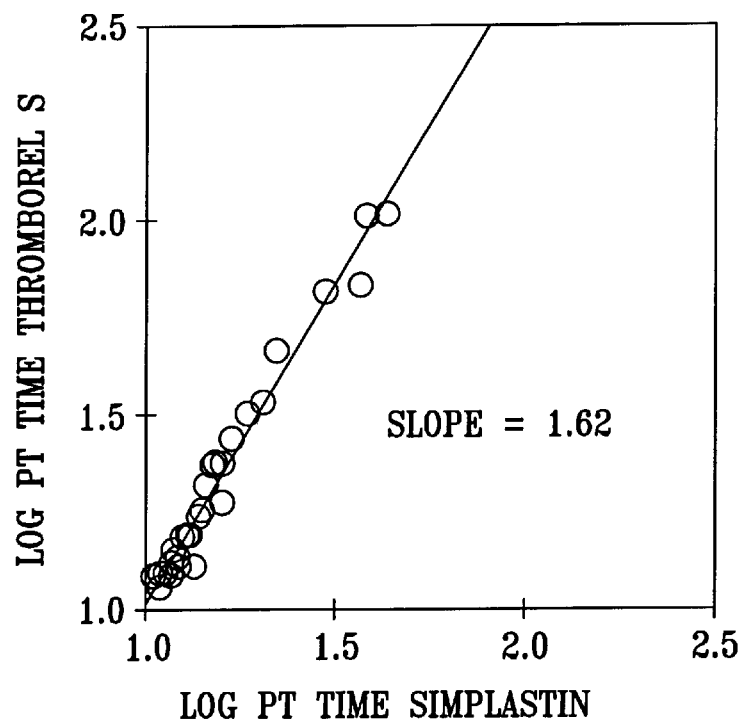

Another method requires no dialysis or detergent removal. Organic solvent was removed from the phophoslipids as described above. The phospholipids were dissolved in 50 mM octyl beta-D-thioglucopyranoside (OTG) to a final concentration of 4 mg/ml. TF, purified as described above, and carrier protein were mixed with the detergent solubilized phospholipids. Enough buffer was added to adjust the final concentrations of TF, carrier protein, phospholipids, and OTG to 10 ug/ml, 1 mg/ml, 4 mg/ml and 10 mM, respectively. $CdCl_2$ was added to a final concentration of 5 mM to activate the TF. The resulting mixed micelles of TF, detergent, and phospholipids were diluted with 20 mM HEPES, pH 7.5, 150 mM NaCl (HBS), containing 0.3 mg/ml phospholipids, to yield a solution containing TF at approximately 0.5 to 1 ug/ml, phospholipids at approximately 500 to 700 ug/ml, and bovine gamma globulin at 25 to 50 ug/ml. This dilution resulted in a reagent with the sensitivities to extrinsic coagulation factors present in control plasmas as presented in Table II. The prothrombin times increase in response to depletion of extrinsic clotting factors in the control plasmas. This sensitivity to clotting factor activity depression is also evident when plasmas from patients undergoing oral anticoagulant therapy are tested (FIG. 2). Plasmas from normal individuals and patients undergoing oral anticoagulant therapy were obtained from a local hospital and snap frozen. PT times for each plasma were determined using the rTF PT reagent, Thromborel S, and Simplastin. The logarithm of the PT times obtained using rTF PT reagent and Simplastin were plotted against the logarithm of the PT time obtained using Thromborel S. When two PT reagents are compared as in FIG. 2, identical sensitivities are depicted as a line having a slope of one. In the case of rTF PT reagent and Thromborel S, the slope is 0.81, indicating that the rTF PT reagent is approximately 20% more sensitive than Thromborel S. However, the slope of the line observed in the graph comparing Simplastin and Thromborel S is 1.62, indicating that Simplastin is much less sensitive than Thromborel S.

The present invention exhibits increased sensitivity to depressed activity levels of factors involved in the extrinsic coagulation cascade. The increased sensitivity of the rTF PT reagent will lessen complications arising in oral anticoagulant therapy and allow for more accurate assessment of specific extrinsic factor deficiencies in patients with bleeding disorders.

The invention now being fully described, it will be apparent to one of ordinary skill in the art that many changes and modifications can be made without departing from the spirit or scope of the invention.

TABLE I

Prothrombin Times of PT Reagent Prepared by Dialysis Using Various Ratios of Phospholipids

| Ratio of Phospholipids (PC:PE:PS)[a] | NHP[b] | Average PT times in seconds | | |
|---|---|---|---|---|
| | | Level I[c] | Level II | Level III |
| 1:1:1 | 13.5 | 13.8 | 25.9 | 49.0 |
| 1:1:0 | 60.0 | 164.2 | 108.1 | 246.1 |
| 1:0:1 | 12.6 | 14.7 | 30.4 | 52.7 |
| 3:1:1 | 13.4 | 19.5 | 53.4 | 69.9 |
| 3:1:0 | 77.5 | 229.4 | —[d] | 231.1 |
| 3:0:1 | 17.3 | 27.5 | 70.1 | 98.2 |
| 5:1:1 | 11.1 | 13.1 | 35.2 | 65.4 |
| 5:0:1 | 10.7 | 13.5 | 34.8 | 66.1 |
| 10:1:1 | 12.4 | 16.4 | 48.4 | 89.2 |
| 10:0:1 | 14.9 | 21.0 | 62.7 | 112.6 |
| 20:1:1 | 18.4 | 27.5 | 82.9 | 147.6 |

[a]The ratio of phospholipids is expressed as the mole ratio of phosphatidylcholine to phosphatidylethanolamine to phosphatidylserine, respectively.
[b]Normal human pool (NHP) is composed of plasma pooled from 10 normal individuals, divided into small aliquots and snap frozen.
[c]Level I, II and III are Thromboscreen control plasmas (Curtin Matheson Scientific, Yorba Linda, Ca) and are designed to simulate patients undergoing 3 different levels or intensity of oral anticoagulant therapy.
[d]This time was greater than 300 sec.

TABLE II

Prothrombin Times with Control Plasmas Using Corvas rTF PT Reagent Prepared without Dialysis[a]

| Plasma Sample | Average PT time in seconds |
|---|---|
| Normal human plasma pool | 12.5 |
| Thromboscreen Control Plasmas: | |
| Level I | 13.7 |
| Level II | 37.1 |
| Level III | 81.1 |

[a]Normal human pool and Thromboscreen control plasmas are described in the footnote to Table I. Handling of the PT reagent is described in the text.

What is claimed is:

1. A method for incorporating active substantially purified natural or recombinant tissue factor into a lipid bilayer of phospholipid liposomes comprising the steps of:

(a) co-solubilizing purified phospholipids, substantially purified tissue factor, and carrier proteins with detergent and cryopreservative agent and thereby causing formation of mixed micelles of phospholipids, tissue factor, carrier proteins, detergent and cryopreservative agent;

(b) removing detergent and thereby causing the micelles to form liposomes; and (c) adding cadmium salt.

2. The method according to claim 1, wherein the phospholipids are phosphatidylcholine, phosphatidylethanolamine, and phosphatidylserine.

3. The method according to claim 1, wherein the detergent is selected form the group consisting of CHAPS, octyl beta-D-glucopyranoside, and octyl beta-D-thioglucopyranoside.

4. The method according to claim 1, wherein the detergent is removed by the technique selected from the group consisting of dialysis, tangential flow diafiltration, and chromatographic means.

5. A method for incorporating substantially purified active natural or recombinant tissue into phospholipid micelles comprising the steps of:
(a) co-solubilizing purified phospholipids, substantially purified tissue factor, and carrier proteins with detergent and thereby causing formation of mixed micelles of phospholipids, tissue factor, carrier proteins, and detergent; and
(b) adding cadmium salt to said micelles, wherein the detergent is not removed from the mixed micelles.

6. The method according to claim 5, wherein the phospholipids are phosphatidylcholine, phosphatidylethanolamine, and phosphatidylserine.

7. The method according to claim 5, wherein the detergent is octyl beta-D-glucopyranoside or octyl beta-D-thioglucopyranoside.

* * * * *